US011344234B2

(12) United States Patent
Trattler et al.

(10) Patent No.: US 11,344,234 B2
(45) Date of Patent: May 31, 2022

(54) CIRCUIT ARRANGEMENT FOR AN OPTICAL MONITORING SYSTEM AND METHOD FOR OPTICAL MONITORING

(71) Applicant: ams AG, Premstaetten (AT)

(72) Inventors: Peter Trattler, Seiersberg-Pirka (AT); Karl Georg Waser, Premstaetten (AT); Herbert Lenhard, Graz (AT)

(73) Assignee: AMS AG, Premstaetten (AT)

( * ) Notice: Subject to any disclaimer, the term of this patent is extended or adjusted under 35 U.S.C. 154(b) by 235 days.

(21) Appl. No.: 16/614,457

(22) PCT Filed: May 15, 2018

(86) PCT No.: PCT/EP2018/062510
§ 371 (c)(1),
(2) Date: Nov. 18, 2019

(87) PCT Pub. No.: WO2018/215240
PCT Pub. Date: Nov. 29, 2018

(65) Prior Publication Data
US 2020/0178865 A1    Jun. 11, 2020

(30) Foreign Application Priority Data
May 23, 2017  (EP) ..................................... 17172553

(51) Int. Cl.
*A61B 5/1455*  (2006.01)
*A61B 5/00*  (2006.01)
(Continued)

(52) U.S. Cl.
CPC ........ *A61B 5/14552* (2013.01); *A61B 5/7225* (2013.01); *G01J 1/44* (2013.01);
(Continued)

(58) Field of Classification Search
CPC ...... A61B 5/14552; A61B 5/7225; G01J 1/44; G01J 2001/4242; G01J 2001/444; G01J 2001/446
See application file for complete search history.

(56) References Cited

U.S. PATENT DOCUMENTS 3,994,590 A    11/1976  Di Martini et al.
5,515,847 A *   5/1996  Braig ................. A61B 5/14532
                                                         600/316
(Continued)

FOREIGN PATENT DOCUMENTS

CN        1937952 A        3/2007
CN       103596492 A        2/2014
(Continued)

OTHER PUBLICATIONS

European Patent Office for International Search Report for PCT/EP2018/062510 dated Jul. 23, 2018.
(Continued)

*Primary Examiner* — Thanh Luu
*Assistant Examiner* — Monica T Taba
(74) *Attorney, Agent, or Firm* — MH2 Technology Law Group LLP (57) ABSTRACT

A circuit arrangement for an optical monitoring system comprises a driver circuit which is configured to generate at least one driving signal for driving the light source. A detector terminal is arranged for receiving a detector current from an optical detector. A gain stage is connected at its input side to the driver circuit for receiving the driving signal and generates a noise signal depending on the driving signal. A processing unit is configured to generate an output signal depending on the detector current and the noise signal.

17 Claims, 4 Drawing Sheets

(51) Int. Cl.
*G01J 1/44* (2006.01)
*G01J 1/42* (2006.01)
(52) U.S. Cl.
CPC . *G01J 2001/4242* (2013.01); *G01J 2001/444* (2013.01); *G01J 2001/446* (2013.01)

(56) References Cited

U.S. PATENT DOCUMENTS

2012/0203077 A1* 8/2012 He .................. A61B 5/6815
    600/301
2017/0099711 A1* 4/2017 Polley ............... H05B 45/37
2018/0085039 A1* 3/2018 Schipper ........... A61B 5/7203

FOREIGN PATENT DOCUMENTS

| | | |
|---|---|---|
| CN | 105910632 A | 8/2016 |
| CN | 106559095 A | 4/2017 |
| EP | 3135196 | 3/2017 |
| WO | 2005/082241 | 9/2005 |
| WO | 2016/156341 | 10/2016 |
| WO | 2017032664 A1 | 3/2017 |

OTHER PUBLICATIONS

Liang, Jie (CN Examiner), Chinese Search Report dated Sep. 23, 2021 for corresponding CN Application No. 2018800333699, 4 pages (with English Translation).

* cited by examiner

CIRCUIT ARRANGEMENT FOR AN OPTICAL MONITORING SYSTEM AND METHOD FOR OPTICAL MONITORING

The invention relates to a circuit arrangement for an optical monitoring system and to a method for optical monitoring. The proposed concept can be applied for monitoring or measuring a biological parameter.

BACKGROUND OF THE INVENTION

Optical sensors find increased use in such diverse fields of application as detection of ambient light, digital color, proximity detection, light-to-digital (LTD), light-to-voltage (LTV) and light-to-frequency (LTF) conversion, in addition to linear sensor arrays for intelligent light sensing in display management for display-based products such as cell phones, TVs, tablets, computer monitors, etc., medical diagnostic equipment, industrial processes and controls, LED solid state lighting, consumer/commercial printer and health/fitness products. Lately optical sensing has been applied to the field of photoplethysmography, PPG, and can be used for monitoring or measuring biological parameters such as heart rate, pulse rate variability or oxygen saturation in the blood.

PPG signals are often obtained by coupling light into a target region of a person's skin, for example by means of a light emitting diode, LED, and measuring a reflected and/or transmitted signal in close proximity to where the light signal has been injected in the first place. However, PPG systems typically rely on minute physical changes in the thickness or volume of blood vessels. Consequently, the obtained PPG signal may have a rather high DC or average component but a comparably low AC or fluctuating component. A typical PPG signal obtained from light injection at the wrist of a person and corresponding measurement has a modulation index in the order of a fraction of 1%, for example in the order of 0.05%-0.3%. Therefore, signal quality of the PPG signal may be of importance for monitoring or measuring biological parameters by means of PPG.

Furthermore, the low AC or fluctuating components which are characteristic for biosensor (PPG) applications, such as heart rate measurements, HRM, are prone to noise. Important contributions to noise are found to be in the frequency range of 0.5 Hz to 4.0 Hz, which represent 30 to 240 beats per minute, BPM, and higher, especially for heart rate variability, HRV, measurements which approximately have sampling rates of some 250 Hz and above. Therefore frequency modulation and demodulation are often used in order to avoid 1/f noise sources to end up in the PPG output signal. Unfortunately, modulation and demodulation does not cancel all noise sources. Measurements and simulation show that a current source or sink noise related to light emission may be a dominant noise source for the whole system. In order to improve signal quality of the PPG signal there is a need to further reduce noise.

SUMMARY OF THE INVENTION

It is to be understood that any feature described hereinafter in relation to any one embodiment may be used alone, or in combination with other features described hereinafter, and may also be used in combination with one or more features of any other of the embodiments, or any combination of any other of the embodiments, unless explicitly described as an alternative. Furthermore, equivalents and modifications not described below may also be employed without departing from the scope of the circuit arrangement for an optical monitoring system and the method for optical monitoring as defined in the accompanying claims.

The following relates an improved concept for optical monitoring of a biological parameter, for example by means of PPG. The concept allows for an improved signal quality of a PPG signal, for example. For example, ways are suggested that allow for reducing signal noise resulting in an improved signal-to-noise ratio and, thus, improved signal quality.

According to the improved concept, a gain stage, for example, a low noise and stabilized gain stage, e.g. a chopper amplifier, is connected to a PPG system. The gain stage generates a noise signal that can be used in various ways to obtain a reduction of a noise component in an output signal of the PPG system. For example, the noise signal can be used as a reference input to an analog-to-digital converter which support noise cancellation in analog-to-digital conversion of the output signal. In other examples, the analog-to-digital converter alternatively samples a PPG signal, such as a detector current, and the noise signal. A noise reduced output signal can be derived from the various sampled signals. Consequently, the output signal has lower noise component and signal-to-noise ratio can be improved. In at least one embodiment a circuit arrangement for an optical monitoring system is provided. The circuit arrangement comprises a driver circuit which is configured to generate at least one driving signal for driving a light source. Furthermore, the circuit arrangement comprises a detector terminal for receiving a detector signal, such as a detector current, e.g. from an optical detector. The circuit arrangement further comprises a gain stage which at its input side is connected to the driver circuit for receiving the driving signal. The gain stage is arranged for generating a noise signal depending on the driving signal. Finally, a processing unit is configured to generate an output signal depending on the detector current and the noise signal.

For example, the processing unit can use the noise signal provided by the gain stage to cancel a noise component in the output signal. Alternatively, or in addition, the processing unit can use the noise signal to reduce the noise component, e.g. by data processing such as subtracting or dividing the output signal with the noise signal.

The optical monitoring system may be a photoplethysmography, PPG, system for monitoring and/or measuring a biological parameter, for example. For example, the optical monitoring system may be a heart rate monitoring, HRM, system, for measuring and/or monitoring a heart rate, a pulse or heart rate variability, PRV or HRV, a system for measuring and/or monitoring a pulse or heart rate variability and/or a pulse oximetry system for measuring and/or monitoring oxygen saturation, SpO2, in blood.

The term "light" refers to electromagnetic radiation in general and to visible light, VIS, ultraviolet radiation, UV, and/or infrared radiation, IR, for example. The light source is configured to emit light with at least one specified wavelength spectrum or one or more spectral lines in the UV, VIS, or IR, for example. The specified wavelength spectrum or spectral line may for example correspond to a spectral band in the green or a spectral line such as 525 nm, which may result in an improved output signal.

The term "optical" is relates to electromagnetic radiation which can be described by geometrical (or ray) optics and physical (or wave) optics. This involves UV, VIS, or IR radiation, for example. For example, the optical monitoring system may operate based on generation, detection and/or processing of such electromagnetic radiation.

In at least one embodiment the processing unit comprises an amplifier circuit with an input side connected to the detector terminal. A demodulation and signal processing unit is connected to an output side of the amplifier circuit. Furthermore, an analog-to-digital converter is connected to an output side of the demodulation and signal processing unit.

In at least one embodiment the amplifier circuit is implemented and connected as a transimpedance amplifier. The amplifier circuit has a first input connected to the detector terminal and a second input connected to a reference terminal. The demodulation and signal processing unit comprises a first band pass filter, a synchronous demodulator, and the second band pass filter which are connected in series.

In at least one embodiment the gain stage comprises a chopper amplifier or a differential amplifier.

In at least one embodiment the reference generator is configured to generate a reference signal with known frequency and phase. The driving circuit comprises a control input which is connected to the reference generator. The demodulation and signal processing unit comprises a signal input which is connected to the reference generator.

In at least one embodiment a signal and hold switch is connected between the driving circuit and the input side of the gain stage. A switch control input is coupled to the demodulation and signal processing unit, the reference generator and the control input.

In at least one embodiment an output side of the gain stage is connected to a reference input of the analog-to-digital converter. The analog-to-digital converter receives the noise signal as a reference for the analog-to-digital converter.

In at least one embodiment a first input select switch is coupled between the demodulation and signal processing unit and the analog-to-digital converter. In a first switching state, the first input select switch electrically connects the demodulation and signal processing unit to the analog-to-digital converter. In a second switching state, the first input select switch electrically connects the gain stage and the analog-to-digital converter.

By means of the switching states corresponding intermediate signals can be generated, e.g. a first signal derived from the detector signal (and including one or more noise components) and a second signal derived from the noise signal provided by the gain stage. The processing unit records the signals separately and may then process them independently. For example, the processing unit can be arranged to apply mathematical operations on the signal such as subtracting and/or dividing the signals from each other.

In at least one embodiment a second input select switch is coupled between the signal and hold switch and the gain stage. In a third switching state, and the second input select switch electrically connects the driving circuit and the gain stage. In a fourth switching state, the second input select switch electrically connects a reference potential to the gain stage.

By means of the switching states of the first and second input select switches corresponding intermediate signals can be generated, e.g. a first signal derived from the detector signal (and including one or more noise components) and a second signal derived from the noise signal (including noise components such as the noise of the gain stage) provided by the gain stage and a third signal including a noise component of the reference potential such as ground. The processing unit records the signals separately and may then process them independently. For example, the processing unit can be arranged to apply mathematical operations on the signal such as subtracting and/or dividing the signals from each other.

In at least one embodiment a control and processing unit is connected to an output side of the analog-to-digital converter and coupled to the first and/or second switch. Furthermore, the control and processing unit is arranged to control the switching states of the first and/or second switch. For example, sets the switching states of the first and/or second input select switch, records the corresponding intermediate signals and processes the intermediate signal, e.g. by applying mathematical operations such as subtracting and/or dividing the signals from each other as discussed above. In some embodiments the control and processing unit comprises a microcontroller or processor and its operation is determined by software. In yet other embodiments the control and processing unit comprises control logic and/or an application-specific integrated circuit, ASIC, or custom chip, such that operation of the control and processing unit is determined by hardware.

In at least one embodiment the light source is not comprised by the circuit arrangement. In at least one embodiment the optical detector is not comprised by the circuit arrangement. For example, the circuit arrangement and/or the driver circuit may be adapted to operate in combination with different types of light sources and/or optical detectors.

In at least one embodiment the optical detector comprises at least one photodetector, for example a photodiode.

In at least one embodiment the circuit arrangement comprises the light source and the light source comprises at least one optical emitter configured and arranged to be driven by at least one driving signal.

In at least one embodiment the at least one optical emitter comprises at least one LED and/or a laser diode.

In at least one embodiment the at least one optical emitter and/or the at least one LED is configured to emit visible light, for example red visible light, green visible light, blue visible light, yellow visible light or visible light with another color and/or spectrum, and/or infrared radiation. Other examples include surface emitting laser diodes such as vertical-cavity surface-emitting laser, VCSEL. Such laser diodes may emit in the VIS or IR, for example, or may even provide the possibility to tune their emission within a desired spectral band.

In at least one embodiment the light source comprises a plurality of optical emitters, for example a plurality of LEDs, wherein different optical emitters of the plurality of optical emitters are configured to emit light of the same or of different spectra.

In at least one embodiment each of the optical emitters comprised by the light source is associated to one of the at least one driving signal and is driven by the associated driving signal.

According to the improved concept, also a method for optical monitoring is provided. The method comprises generating at least one driving signal, for example at least one driving current, for driving a light source and receiving a detector current from an optical detector. Furthermore, a noise signal is generated depending on the at least one driving signal. Finally, an output signal is generated depending on the noise signal and the detector current from an optical detector.

The optical monitoring may comprise heart rate monitoring, HRM, pulse or heart rate variability, PRV, monitoring, and/or pulse oximetry, SpO2.

In at least one embodiment the method further comprises illuminating a target region of an object by means of light emitted by the light source and detecting a fraction of the light being reflected and/or transmitted by the target region and/or a region of the object being adjacent to the target region. The method comprises generating the detector current based on the detected fraction of the light.

According to some implementations of the method the gain stage generates the noise signal which can be used in various ways to obtain reduction of a noise component in an output signal of the PPG system. For example, the noise signal can be used as a reference input to an analog-to-digital converter which support noise cancellation in analog-to-digital conversion of the output signal. In other examples, the analog-to-digital converter alternatively samples a PPG signal, such as a detector current, and the noise signal. A noise reduced output signal can be derived from the various samples. Consequently, the output signal has lower noise component and signal to noise ratio can be improved.

Further embodiments of the method are readily derived from the various implementations and embodiments of the circuit arrangement and vice versa.

In the following, the principle presented above is described in further detail with respect to drawings, in which exemplary embodiments are presented.

In the exemplary embodiments and Figures below, similar or identical elements may each be provided with the same reference numerals. The elements illustrated in the drawings and their size relationships among one another, however, should not be regarded as true to scale. Rather individual elements, such as layers, components, and regions, may be exaggerated to enable better illustration or improved understanding.

DETAILED DESCRIPTION

Figure 1:
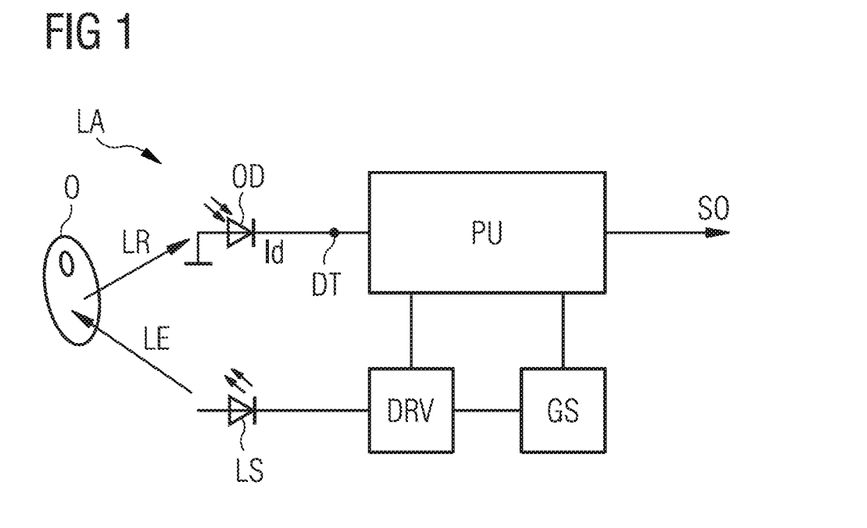
FIG. 1 shows an exemplary embodiment of a circuit arrangement for an optical monitoring system.

FIG. 1 shows an exemplary embodiment of a circuit arrangement for an optical monitoring system.

The circuit arrangement comprises a driver circuit DRV, a processing unit PU, which is connected to the driver circuit DRV and to a detector terminal DT, and further comprises a gain stage GS, which, at its input side, is connected to the DT driver circuit DRV and which, at its output side, is connected to the processing unit PU. Furthermore, an optical detector OD connected to the detector terminal DT as well as a light source LS connected to the driver circuit DRV are shown in the drawing. The optical detector OD and the light source LS may be comprised by the circuit arrangement. In alternative embodiments the optical detector OD and/or the light source LS are not comprised by circuit arrangement. For example, the circuit arrangement can be integrated as an integrated circuit, IC, e.g. by means of a CMOS process. The integrated circuit, IC, may comprise the optical detector OD as an integrated component. In other embodiments, however, the optical detector OD and/or the light source LS may be connected to the IC as external components, e.g. arranged in a common sensor package.

The drawing also indicates an external object O as well as an emitted light LE, response light LR and ambient light LA. The object O may be a body part or even a part of a body part of a person or an animal. The object O may be a wrist of a person, for example. During operation, the circuit arrangement and/or the light source LS and the optical detector OD can be arranged in close proximity or in contact to the object O.

The driver circuit DRV is arranged to generate a driving signal for driving the light source LS. The driver circuit DRV may also be arranged to generate a plurality of driving signals for driving the light source LS or several light sources. For example, the driving signal or the plurality of driving signals may correspond to a driving current or a plurality of driving currents, respectively. In response to the driving signal, the light source LS emits light LE to illuminates a target region of the object O. In this embodiment, the driving signal is a pulsed signal that changes back and forth between an off-level and an on-level. In turn, the light source LS is activated in a pulsed manner as well. For example, when the driving signal assumes the on-level, the light source LS is activated, i.e. emits light LE. When the driving signal assumes the off-level, e.g. having a driving current equal to or essentially equal to zero, the light source LS is not activated, i.e. does not emit light. As a consequence the emitted light LE is also pulsed with on-phases when the driving signal assumes the on-level and off-phases when the driving signal assumes the off-level, i.e. the light source LS changes back and forth between emission and no emission of light, respectively.

The driving signal can be characterized by a pulse frequency. For optical monitoring applications the pulse frequency lies between several Hz and several kHz, for example between 20 Hz and 1 kHz. In some embodiments, the pulse frequency can be adjustable. Consequently, a switching frequency of the light source LS, e.g. a frequency of switching between the off-phase and the on-phase, corresponds approximately to the pulse frequency of the driving signal.

The emitted light LE eventually strikes the target region of the object O. Different events may occur at the target region. For example, a fraction of light gets reflected or scattered by the object O. Another fraction may couple inside the object O, e.g. a tissue of a person, and gets reflected or scattered inside and again coupled out of the object. These events result in a response light LR which is transmitted by the object.

For example, the response light LR can be detected by the optical detector OD. The optical detector OD is implemented as a photodetector which is sensitive in the UV, VIS and/or IR. Typically, the optical detector OD is sensitive to the light LE being emitted by the light source LS. The optical detector OD comprises a single photodiode or several photodiodes, e.g. arranged as an array of photodetectors. Single or several photodiodes may have one or several different optical filters to filter only the light which is emitted by the light source(s) LS. This allows for attenuating ambient light, for example.

In addition to the response light LR, the optical detector OD may also detect ambient light LA. Ambient light LA originates from sources of light that are already available naturally (e.g. the sun, moon, lightning) or from artificial light already being used (e.g. to light a room) and that may or may not be present in an environment of the circuit arrangement and/or the object O.

Regardless the origin of incident light, the optical detector generates a detector signal, e.g. based on the detected response light LR and/or the detected ambient light LA. If the optical detector is implemented as one or more photodiodes the optical detector OD generates a detector current Id at the detector terminal DT. At the detector terminal DT, the detector current Id is supplied to the processing unit PU as input current.

A signal-to-noise ratio of the output signal SO has a signal component and a noise component. The signal component is largely determined by the detector current Id. The noise component, however, depends on various sources. For example, the driving signal, such as the driving current or plurality of driving currents, is prone to signal noise. Signal noise may propagate and influence other signals in the circuit arrangement. For example, as the driving signal drives the light source LS a noise component in the driving signal will influence the emitted light LE, and consequently also the response light LR. Ultimately, the noise component may also have an impact on the detector signal and the output signal SO. In fact, measurements and simulation on the circuit arrangement presented this far show that a noise component related to light emission based on the driving signal may be a dominant noise source for the whole system.

The gain stage GS receives the driving signal from the driver circuit DRV and is configured to generate a noise signal based on the driving signal. The noise signal is a measure of the noise component, e.g. of the driving signal. For example, the gain stage GS is a low noise and stabilized gain stage.

The processing unit PU receives the detector current Id as input current and the noise signal as a reference input. The processing unit PU then generates an output signal SO based on the detector current Id and the reference signal. In fact, as the noise signal is used as a reference, the impact of the noise component, e.g. due to noise in the driving signal, can be cancelled or at least reduced. Thus, the output signal SO has higher signal quality due to noise reduction. The output signal SO is a photoplethysmogram, PPG, signal or a signal suitable for generating a PPG signal, for example.

The detector signal, or detector current, typically reflects whether the driving signal assumes the on-level or the off-level. In other embodiments (not shown) this can be used to account for the impact of ambient light. For example, when the driving signal assumes the on-level the optical detector OD typically detects a superposition of response light LR and ambient light LA. If, however, the driving signal assumes the off-level, the optical detector OD typically detects only a contribution of ambient light LA as there is no response light LR due to emission of the light source LS. The processing unit PU, or additional components such as a microprocessor, can be arranged to process the detector signal such that a contribution of the ambient light LA can be determined. For example, a difference signal can be determined between the detector signal during on-level and off-level. The difference signal may be used as a measure of the detected ambient light LA.

Figure 2:
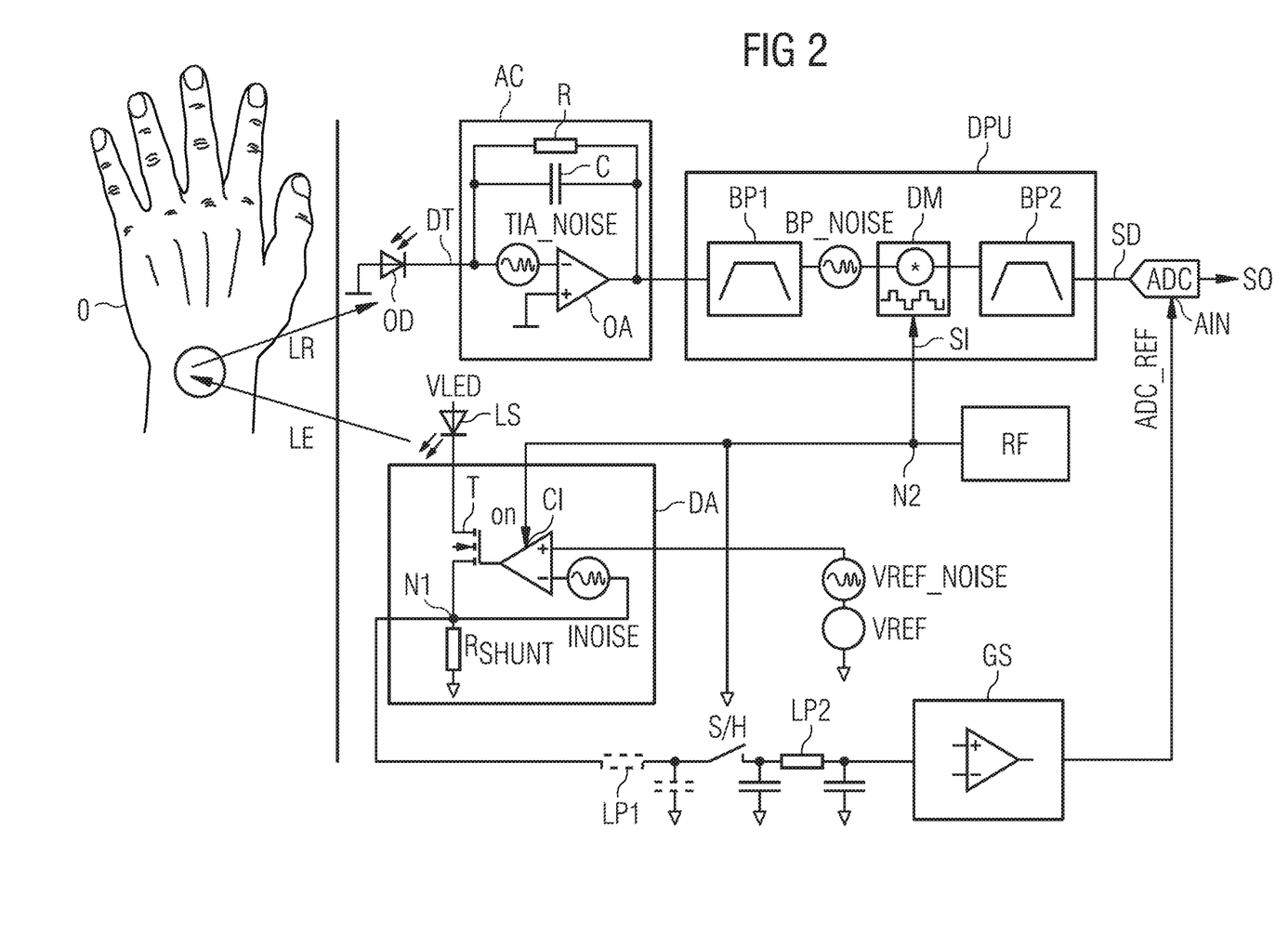
FIG. 2 shows another exemplary embodiment of a circuit arrangement for an optical monitoring system.

FIG. 2 shows another exemplary embodiment of a circuit arrangement for an optical monitoring system. The processing unit PU comprises an amplifier circuit AC with an input side connected to the detector terminal DT, and a demodulation and signal processing unit DPU connected to an output side of the amplifier circuit AC. The processing unit PU also comprises an analog-to-digital converter ADC connected to the demodulation and signal processing unit DPU.

For example, the amplifier circuit AC is implemented and connected as a transimpedance amplifier, TIA, and comprises an operational amplifier OA with a first input, for example an inverting input, connected to the detector terminal DT and with a second input, for example a non-inverting input, connected to a reference terminal. The amplifier circuit AC comprises a capacitor C, such as a tunable capacitor, which is connected between the first input of the operational amplifier OA and an output of the operational amplifier OA. The amplifier circuit AC further comprises a resistor R, such as a tunable resistor, which is connected between the first input and the output of the operational amplifier OA.

In alternative embodiments the amplifier circuit AC comprises only one of the resistor R and the capacitor C. By tuning a resistance of the resistor R and/or a capacitance of the capacitor C, an amplification factor of the amplifier circuit AC may be tuned.

The demodulation and signal processing unit DPU comprises a first band pass filter BP1, a synchronous demodulator DM, and the second band pass filter BP2 all of which are connected in series between the output of the amplifier circuit AC and the input side of the analog-to-digital converter ADC. The synchronous demodulator DM a signal input SI which is connected to a reference generator RF.

The driver circuit DRV comprises a driver amplifier DA which is implemented and connected as a current sink. The driver amplifier DA comprises a first input, e.g. a positive input, which is connected to a voltage reference VREF. Furthermore, the driver amplifier DA comprises a second input, e.g. a negative input, which is connected to a first circuit node N1. The first circuit node N1 is connected to ground via a shunt resistor Rshunt. A control input CI is connected to a second circuit node N2. The second circuit node N2 is further connected to the synchronous demodulator DM, the reference generator RF and, further, to a signal and hold switch S/H. The first circuit node N1 is connected to the light source LS via a transistor TR. A control side of the transistor TR is connected to an output of the driver amplifier DA.

The first circuit node N1 is further connected to a filter stage. The filter stage comprises a series connection comprising a first low pass filter (optional), the signal and hold switch SH and a second low pass filter. The filter stage is connected to the input side of the gain stage GS via the second low pass filter. In this embodiment the gain stage GS is implemented as a low noise and stabilized chopper amplifier. An output side of the gain stage GS is connected to a reference input AIN of the analog-to-digital converter ADC. For example, the analog-to-digital converter is implemented as an integrating converter such as a sigma-delta converter or a successive approximation converter, SAR-ADC.

Several sources of noise are also indicated in the drawing and are associated with the various circuit components. A reference voltage noise is denoted as VREF_NOISE and attributed with the voltage reference VREF. A current noise INOISE is associated with the current sink. The gain stage GS is not associated with a noise component as the chopper is implemented as a low noise component with negligible noise. Furthermore, the amplifier circuit AC has a noise component denoted as amplifier noise TIA_NOISE. The processing unit noise component is denoted as BP_NOISE and is associated with the demodulation and signal processing unit DPU, e.g. due to bandpass filtering.

The reference generator RF issues a reference signal which is characterized by a pulse frequency. For optical monitoring applications the pulse frequency lies between several Hz and several kHz, for example between 20 Hz and 1 kHz. In some embodiments, the pulse frequency can be adjustable. The reference is applied to the control input of the driving amplifier. As a consequence the driving amplifier DA generates the driving signal, i.e. a driving current as the driving amplifier DA is implemented as a current sink.

The driving current is applied to the light source LS, which in this embodiment is implemented as a LED. In fact, the driving current switches between off-phases and on-phases according to the pulse frequency defined by the reference generator RF. Consequently, a switching frequency of the light source LS, e.g. a frequency of switching between the off-phase and the on-phase corresponds approximately to the pulse frequency of the driving signal. Thus, the light sources LS is switched on- and off as the driving current changes back and forth between the off-phase and the on-phase. The current sink is prone to the current noise INOISE as introduced above. Thus, light emission LE by means of the light source LS is also affected by said noise component.

The response light LR can be detected by the optical detector OD and a detector current Id is generated. The amplifier circuit AC amplifies the detector current Id and generates an intermediate signal which is supplied to the demodulation and signal processing unit DPU. In addition to the current noise already present, the amplifier circuit introduces the amplifier noise TIA_NOISE.

The demodulation and signal processing unit DPU generates a demodulated signal SD based on the intermediate signal. For example, the first band pass filter BP1 filters the intermediate signal according to a first frequency band. The synchronous demodulator DM demodulates the intermediate signal down to a frequency determined by the reference signal supplied by the reference generator. For example, the frequency is chosen to comply with the capabilities of the analog-to-digital converter ADC. The analog-to-digital converter ADC may be arranged for a certain frequency range. The synchronous demodulator DM demodulates the intermediate signal down to a frequency that fits into the frequency range of the analog-to-digital converter ADC. The demodulated signal SD undergoes an optional second band pass filtering by means of the second band pass filter BP2 which filters the demodulated intermediate signal according to a second frequency band. As a consequence of signal processing in the demodulation and signal processing unit DPU another noise component is added to the demodulated signal SD, i.e. the processing unit noise BP_NOISE.

Finally, the demodulated signal SD is supplied to the analog-to-digital converter ADC. The analog-to-digital converter ADC converts for example the analog the modulated signal SD into the digital output signal SO. A corresponding timing or clock of the analog-to-digital converter ADC of the may be controlled or provided by the gain stage GS, i.e. the noise signal.

The gain stage GS receives the driving signal from the driver circuit DRV via the filter stage. The signal and hold switch SH is connected to the reference generator RF and, thus, is controlled by the reference signal as well. Thus, switching of the driving amplifier, i.e. the current sink, and the signal and hold switch is synchronized to the reference signal (as is the demodulation by the synchronous demodulator DM). Consequently, the gain stage GS only receives the driving signal when in on-level, for example. The received driving signal includes the current noise INOISE component. As the gain stage is a low noise and stabilized gain stage additional noise from the gain stage can be neglected.

The chopper is arranged to determine the current noise component INOISE from the driving signal. The noise signal represents the current noise component INOISE and is applied to the reference inout AIN as an ADC reference ADC_REF to the analog-to-digital converter ADC. Thus, the signal including the noise from the current source or current sink is used for the reference input of the analog-to-digital converter ADC. Therefore, it cancels this noise in the signal output SO. The remaining noise components, e.g. TIA_NOISE and BP_NOISE may still be present in the signal output SO. However, it can be shown that these noise components may not be the dominant sources and could even be further reduced by the design of the amplifier circuit AC and/or the demodulation and signal processing unit DPU.

The gain stage GS can be implemented for low frequencies. In fact, the gain stage GS may not have the requirement of fast settling as the current source or current sink. In most cases low noise operation contradicts the requirement of fast speed and power. The signal and hold switch SH will demodulate the driving signal, e.g. a PWM pulsed signal according to the pulse frequency of the reference signal issued by the reference generator RF, such that the noise level in the driving signal is converted to low frequencies which the gain stage GS can process and amplify. The first low pass filter LP1 in the filter stage filters frequencies above the modulation or pulse frequency to avoid folding of these frequencies to lower frequencies in the SH switch. The second low pass filter LP2 may be required depending on the characteristics of the gain stage GS. For example, the second low pass filter LP2 can be arranged to filter high frequency components from the driving signal that otherwise might alias down to lower frequencies. In case the gain stage GS filters such components anyway, the second low pass filter LP2 is optional and generally not required for operation.

Figure 3:
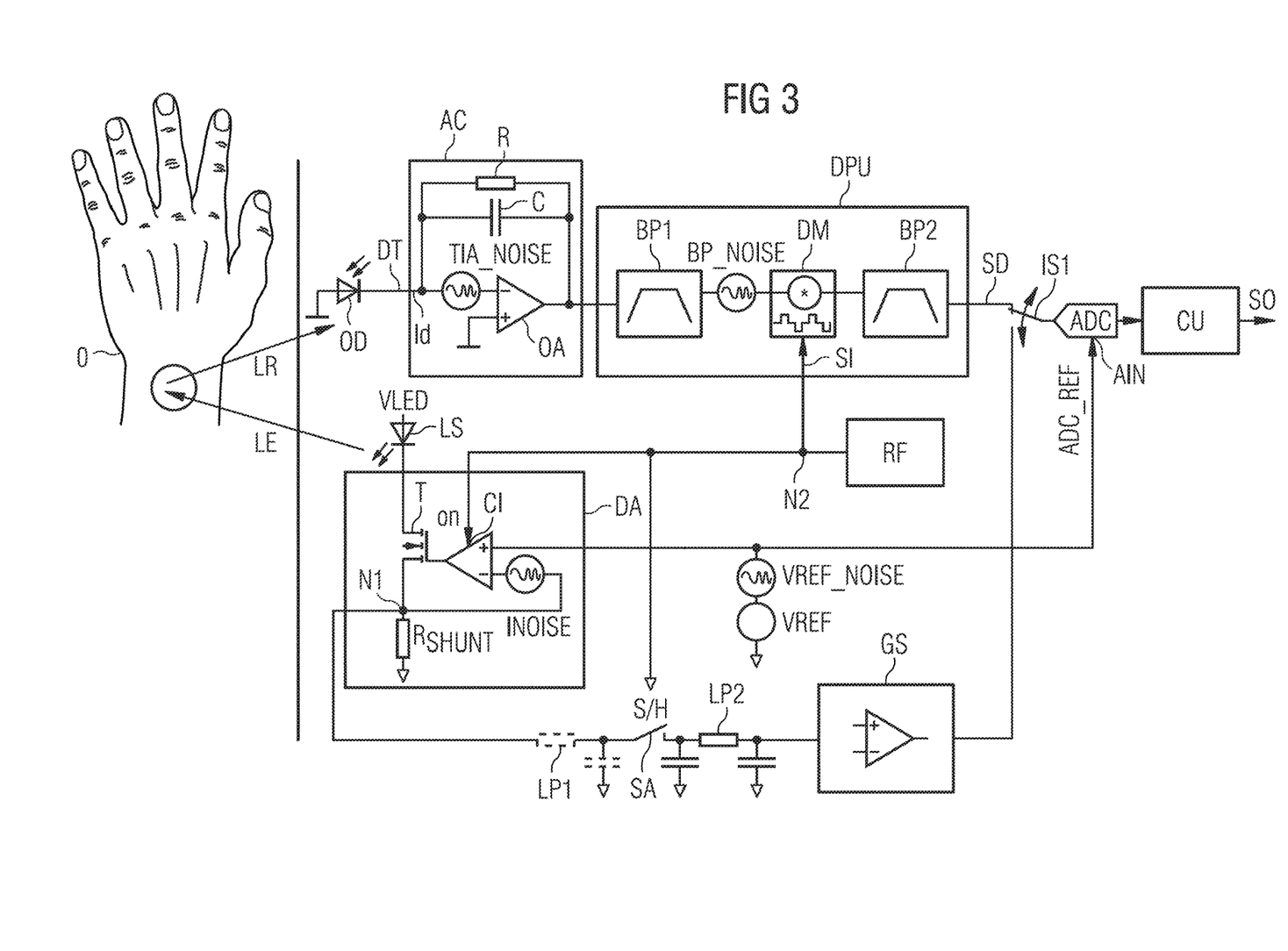
FIG. 3 shows an exemplary embodiment of a circuit arrangement for an optical monitoring system.

FIG. 3 shows another exemplary embodiment of a circuit arrangement for an optical monitoring system. In fact, the embodiment shown in this drawing is based on the one discussed in FIG. 1. The analog-to-digital converter ADC alternatively samples the demodulated signal SD and the noise signal.

In order to achieve this, some modifications over FIG. 1 are introduced. Instead of applying the noise signal to a reference input AIN of the analog-to-digital converter ADC the output side of the gain stage GS is connected to a first input select switch IS1. Said switch IS1 is connected between the second band pass filter BP2 and the analog-to-digital converter ADC. Furthermore, the voltage reference VREF is connected to the reference input of the analog-to-digital converter ADC.

In addition a control and processing unit CU is connected to an output side of the analog-to-digital converter ADC and is coupled to the first input select switch IS1. In fact, the control and processing unit CU is arranged to control the switching states of the first input select switch IS1. For example, it is possible to implement a noise correction in software. In a first switching state the demodulated signal SD including the noise components introduced above is applied to the analog-to-digital converter ADC and converted into the digital output signal SO. This signal may be denoted the (noisy) PPG signal ppg_signal hereinafter. In a second switching state the first input select switch IS1 applies the noise signal from the gain stage to the analog-to-digital converter and converted into a digital representation of the noise signal, denoted curr_sink_signal. This signal derives from the gain stage GS connected to the driving amplifier, e.g. the current sink or current source. The control and processing unit CU executes data manipulation to the signals, e.g. by dividing ppg_signal with curr_ sink_signal a noise component in the PPG signal is cancelled or reduced. This can be implemented in hardware or software.

Figure 4:
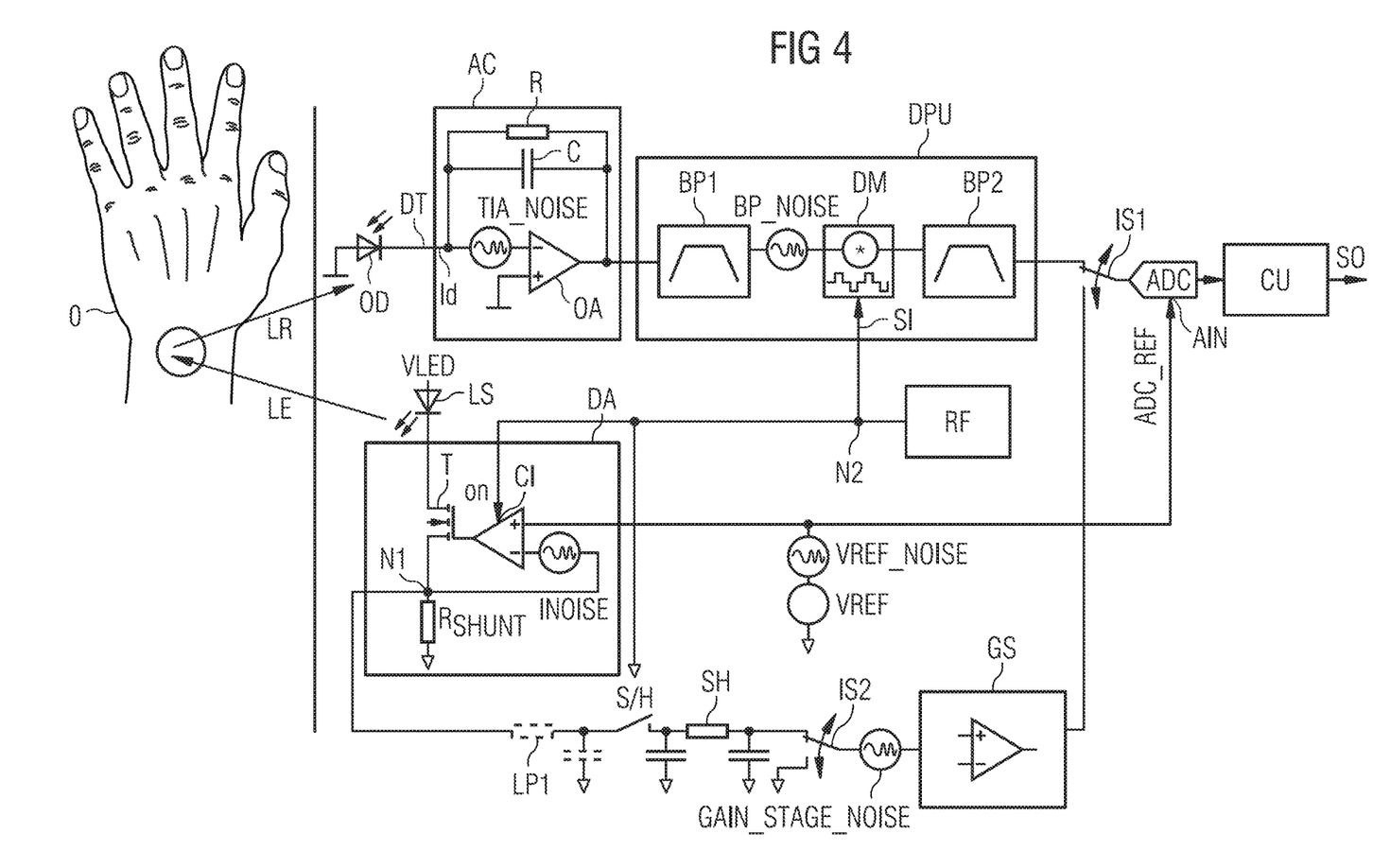
FIG. 4 shows an exemplary embodiment of a circuit arrangement for an optical monitoring system.

FIG. 4 shows another exemplary embodiment of a circuit arrangement for an optical monitoring system. The circuit layout shown in FIG. 3 has an additional feature. The gain stage GS does not have to be built with a higher gain, e.g. to assure that it amplifies the current source noise up to the full range of the analog-to-digital converter ADC. For example, the gain stage GS can be implemented without the requirement of a low 1/f noise simplifying the whole implementation. Instead a second input select switch IS2 can be introduced at the input side of the gain stage GS.

The first and second input select switches are controlled by the control and processing unit CU in a sequence of switching states. For example, the following signals are applied to the analog-to-digital converter ADC in sequence: the PPG signal, ppg_signal, the noise signal, curr_sink_signal, and a reference potential signal, gnd_signal, derived from a switching in which the first and second input select switches IS1, IS2 are switch so as to connect the reference potential GND to the gain stage GS, e.g. by connecting the gain stage input to ground.

This allows for cancelling or reducing the low frequency noise component of the gain stage GS. For example, the noise for the ppg_signal is cancelled with the following formula:

ppg_signal_noise_free=(ppg_signal)/(curr_sink_signal−gnd_signal)

This can be implemented in hardware or software.

One application of the proposed concept are biosensors. They have a signal range in the Hz range, therefore any 1/f noise introduced by the device is problematic for the signal. As these devices are very often portable device, e.g. smart band with heart rate measurement, or smart watch, there often is a demand to reduce the current consumption, e.g. of the HRM measurement. The noise sources in the system are typically the limiting this reduction as the output signal shall have a reasonable SNR to allow accurate HRM measurements. Thus, the proposed concept can also be applied to reducing current consumption in mobile biosensors and biosensor applications.

The invention claimed is:

1. A circuit arrangement for an optical monitoring system, comprising:
   a driver circuit configured to generate at least one driving signal for driving the light source,
   a detector terminal for receiving a detector current from an optical detector,
   a gain stage connected at its input side to the driver circuit for receiving the driving signal and generating a noise signal depending on the driving signal, wherein the gain stage comprises a chopper amplifier or a differential amplifier, and
   a processing unit configured to generate an output signal depending on the detector current and the noise signal.

2. The circuit arrangement according to claim 1, wherein the processing unit comprises
   an amplifier circuit with an input side connected to the detector terminal,
      a demodulation and signal processing unit connected to an output side of the amplifier circuit, and
      an analog-to-digital converter connected to an output side of the demodulation and signal processing unit.

3. The circuit arrangement according to claim 2, wherein the amplifier circuit is implemented and connected as a transimpedance amplifier with a first input connected to the detector terminal and with a second input connected to a reference terminal, and
   the demodulation and signal processing unit comprises an optional first bandpass filter, a synchronous demodulator, and a second bandpass filter connected in series.

4. The circuit arrangement according to claim 2, wherein
   a reference generator is configured to generate a reference signal with a known frequency and phase,
   the driving circuit comprises a control input which is connected to the reference generator, and
   the demodulation and signal processing unit comprises a signal input which is connected to the reference generator.

5. The circuit arrangement according to claim 4, wherein
   a signal and hold switch which is connected between the driving circuit and the input side of the gain stage, and
   a switch control input is coupled to the demodulation and signal processing unit, the reference generator and the control input.

6. The circuit arrangement according to claim 2, wherein an output side of the gain stage is connected to a reference input of the analog-to-digital converter to receive the noise signal as a reference for the analog-to-digital converter.

7. The circuit arrangement according to according to claim 2, wherein
   a first input select switch is coupled between the demodulation and signal processing unit and the analog-to-digital converter,
   wherein in a first switching state the first input select switch electrically connects the demodulation and signal processing unit and the analog-to-digital converter, and
   wherein in a second switching state the first input select switch electrically connects the gain stage and the analog-to-digital converter.

8. The circuit arrangement according to claim 7, wherein
   a second input select switch is coupled between the signal and hold switch and the gain stage,
   wherein in a third switching state the second input select switch electrically connects the driving circuit and the gain stage, and
   wherein in a fourth switching state the second input select switch electrically connects a reference potential to the gain stage.

9. The circuit arrangement according to claim 8, wherein
   a control and processing unit is connected to an output side of the analog-to-digital converter and coupled to the first and/or second input select switch, and wherein the control and processing unit is arranged to control the switching states of the first and/or second switch.

10. The circuit arrangement according to claim 1, further comprising the light source, wherein the light source comprises at least one optical emitter configured and arranged to be driven by the at least one driving signal.

11. The circuit arrangement according to claim 1, further comprising the optical detector.

12. The circuit arrangement according to claim 1, wherein the output signal is a photoplethysmogram, PPG, signal or a signal suitable for generating a PPG signal.

13. The circuit arrangement according to claim 1, wherein the gain stage is an analog gain stage.

14. A method for optical monitoring, the method comprising the steps of:
   generating at least one driving signal for driving a light source,
   receiving a detector current from an optical detector, generating a noise signal with a gain stage depending on the at least one driving signal, wherein the gain stage comprises a chopper amplifier or a differential amplifier, and generating an output signal depending on a combination of the detector current and the noise signal.

15. The method for optical monitoring according to claim 14, wherein the noise signal is an analog signal.

16. The method according to claim 14, further comprising:

illuminating a target region of an object by means of light emitted by the light source, detecting a fraction of the light being reflected from and/or transmitted by the target region and/or a region of the object being adjacent to the target region, and generating the detector current based on the detected fraction of the light.

17. A circuit arrangement for an optical monitoring system, comprising:

a driver circuit configured to generate at least one driving signal for driving a light source, a detector terminal for receiving a detector current from an optical detector, a gain stage connected at its input side to the driver circuit for receiving the driving signal and generating a noise signal depending on the driving signal, a processing unit configured to generate an output signal depending on the detector current and the noise signal, further comprising:

an amplifier circuit with an input side connected to the detector terminal, a demodulation and signal processing unit connected to an output side of the amplifier circuit, and an analog-to-digital converter connected to an output side of the demodulation and signal processing unit; and wherein:

an output side of the gain stage is connected to a reference input of the analog-to-digital converter to receive the noise signal as a reference for the analog-to-digital converter; or wherein:

a first input select switch is coupled between the demodulation and signal processing unit and the analog-to-digital converter, wherein in a first switching state the first input select switch electrically connects the demodulation and signal processing unit and the analog-to-digital converter, and wherein in a second switching state the first input select switch electrically connects the gain stage and the analog-to-digital converter.

* * * * *